United States Patent [19]
Uozumi et al.

[11] Patent Number: 5,298,399
[45] Date of Patent: Mar. 29, 1994

[54] GENE AND PROCESS FOR PRODUCING A THERMOSTABLE UREASE

[75] Inventors: Takeshi Uozumi, Tokyo; Haruhiko Masaki, Chiba; Makoto Hidaka, Tokyo; Akira Nakamura, Kamifukuoka; Michihisa Maeda, Tokyo; Yasuo Yoneta, Yaizu, all of Japan

[73] Assignee: Sapporo Breweries Limited, Tokyo, Japan

[21] Appl. No.: 732,242

[22] Filed: Jul. 18, 1991

[30] Foreign Application Priority Data

Aug. 10, 1990 [JP] Japan .................. 2-10178

[51] Int. Cl.$^5$ ............... C12N 15/57; C12N 15/31; C12N 15/11; C12P 21/00
[52] U.S. Cl. ............... 435/69.1; 435/172.3; 435/227; 435/228; 435/252.33; 536/23.2; 536/23.7
[58] Field of Search ......... 435/69.1, 172.3, 252.33, 435/228, 227, 228; 536/27, 23.2, 23.7

[56] References Cited

U.S. PATENT DOCUMENTS

4,753,882  6/1988  Takashio et al. .............. 435/228

FOREIGN PATENT DOCUMENTS

0229219  7/1987  European Pat. Off.
59-17987  1/1984  Japan.

OTHER PUBLICATIONS

Harry L. T. Mobley et al, "Microbial Ureases: Significance, Regulation, and Molecular Characterization", Microbiological Reviews, vol. 53, 85–108, Mar. 1989.
Bradley D. Jones et al, "*Proteus mirabilis* Urease: Nucleotide Sequence Determination and Comparison with Jack Bean Urease", Journal of Bacteriology, vol. 171, No. 12, 6414–6422, 1989.
Gerhard Morsdorf et al, "Cloning of the genes encoding urease from *Proteus vulgaris* and sequencing of the structural genes", FEMS Microbiology Letters, 67–74, 1990, vol. 66.
Scott B. Mulrooney, "Sequence of the *Klebsiella aerogenes* Urease Genes and Evidence for Accessory Proteins Facilitating Nickel Incorporation", Journal of Bacteriology, vol. 172, No. 10, 5837–5843, 1990.
Kim et al., Kor. J. Appl. Microbiol. Bioeng. 13(3):297–302, 1985; *Biol Abstr* 81(3):AB–393, Ref. No. 23,024, Feb. 1, 1986.
Jones et al., "*Proteus mirabilis* Urease . . . ", *J. Bacter.* 170:3342–3349, Aug. 1988.

*Primary Examiner*—Robert A. Wax
*Assistant Examiner*—Stephen Walsh
*Attorney, Agent, or Firm*—Frishauf, Holtz, Goodman & Woodward

[57] ABSTRACT

An isolated structural Bacillus sp. TB-90 (FERM BP-795) urease gene, which comprises base sequences encoding the amino acid sequences of three subunits of urease. A recombinant DNA comprising Bacillus sp. TB-90 (FERM BP-795) urease gene capable of replicating in *Escherichia coli*. A process for producing urease, which comprises cultivating *Escherichia coli* carrying a recombinant DNA comprising Bacillus sp. TB-90 (FERM BP-795) urease gene capable of replicating in *Escherichia coli* and recovering urease from the culture mixture 12 Claims, 4 Drawing Sheets Ac:AccI   E:EcoRI   Pm:PmaCI
Bl:BalI   H:HindIII   Sm:SmaI
Bm:BamHI   Nh:NheI   Sp:SphI ▨ duplex area

FIG. 4

Urease gene and operon

| plasmid | T β α 2 3 4 5 7 | Urease Activity U/mg | U/ml |
|---|---|---|---|
| pUM011 | NhoI ... BamHI HincII SphI SacI | 122 | 56.7 |
| pUM262 | | 46.1 | 23.3 |
| pUM212 | | 0.0 | 0.0 |
| pUM222 | | 0.0 | 0.0 |
| pUM242 | | 0.07 | 0.02 |

—//— frame shift

GENE AND PROCESS FOR PRODUCING A THERMOSTABLE UREASE

BACKGROUND OF THE INVENTION

The present invention relates to a novel isolated structural gene of urease, to a recombinant DNA capable of replicating in *Escherichia coli* carrying a vector into which said structural gene has been introduced, and to a process for producing urease, which comprises cultivating *Escherichia coli* carrying said recombinant DNA and recovering urease from the culture mixture.

Urease (EC 3.5.1.5) is an enzyme which catalyzes decomposition of urea to form ammonia and carbon dioxide, and is widely found in plants, animals and microorganisms.

Those derived from jack beans (*Canavalia ensiformic*) and from microorganisms have already been produced industrially (Japanese Patent Kokai No.86081/1983 and No.17987/1984) and are used as a drug for clinical diagnosis.

In addition, structural genes have been reported with the urease derived from *Proteus mirabilis*, [Bradley D. Jones & Harry L. T. Mobley; J. Bacteriol., 171, 6414-6422 (1989)], *Staphylococcus saprophyticus* [Soren Garermann & Reihard Marre; Infect. Immun., 57, 2998-3002 (1989)], *Klebsiella pneumoniae* [Gerald F. Gerlach, et al.; FEMS Microbiol. Lett., 50, 131-135 (1983)], *Providencia stuartii* [Harry L. T. Mobley, et al.; Infect. Immun., 54, 161-169 (1986)], *Escherichia coli* [Carleen M. Collins & Stanley Falkow; J. Bacteriol., 170, 1041-1045 (1988)], and *Bacillus pasteurii* [Kor. J. Appl. Microbiol. Bioeng., 13, 297-302 (1985)]. Expression of urease gene in *Escherichia coli* is reported with *Staphylococcus saprophyticus*, *Klebsiella pneumoniae*, *Providencia stuartii* and *Bacillus pasteurii* among the literatures shown above.

The present inventors formerly reported a novel urease more stable than known enzymes [Japanese Patent Kokai No.175174/1987].

However, production of said highly stable urease utilizing the techniques of genetic engineering has not been reported yet.

SUMMARY OF THE INVENTION

The present invention relates to a novel isolated structure gene of urease, to a recombinant DNA capable of replicating in *Escherichia coli* carrying a vector into which said structural gene has been introduced, and to a process for producing urease, which comprises cultivating *Escherichia coli* carrying said recombinant DNA and recovering urease from the culture mixture.

BRIEF DESCRIPTION OF THE DRAWINGS

FIG. 4 is a schematic drawing which depicts the activity and protein content of plasmids

DETAILED DESCRIPTION OF THE INVENTION

Figure 1:
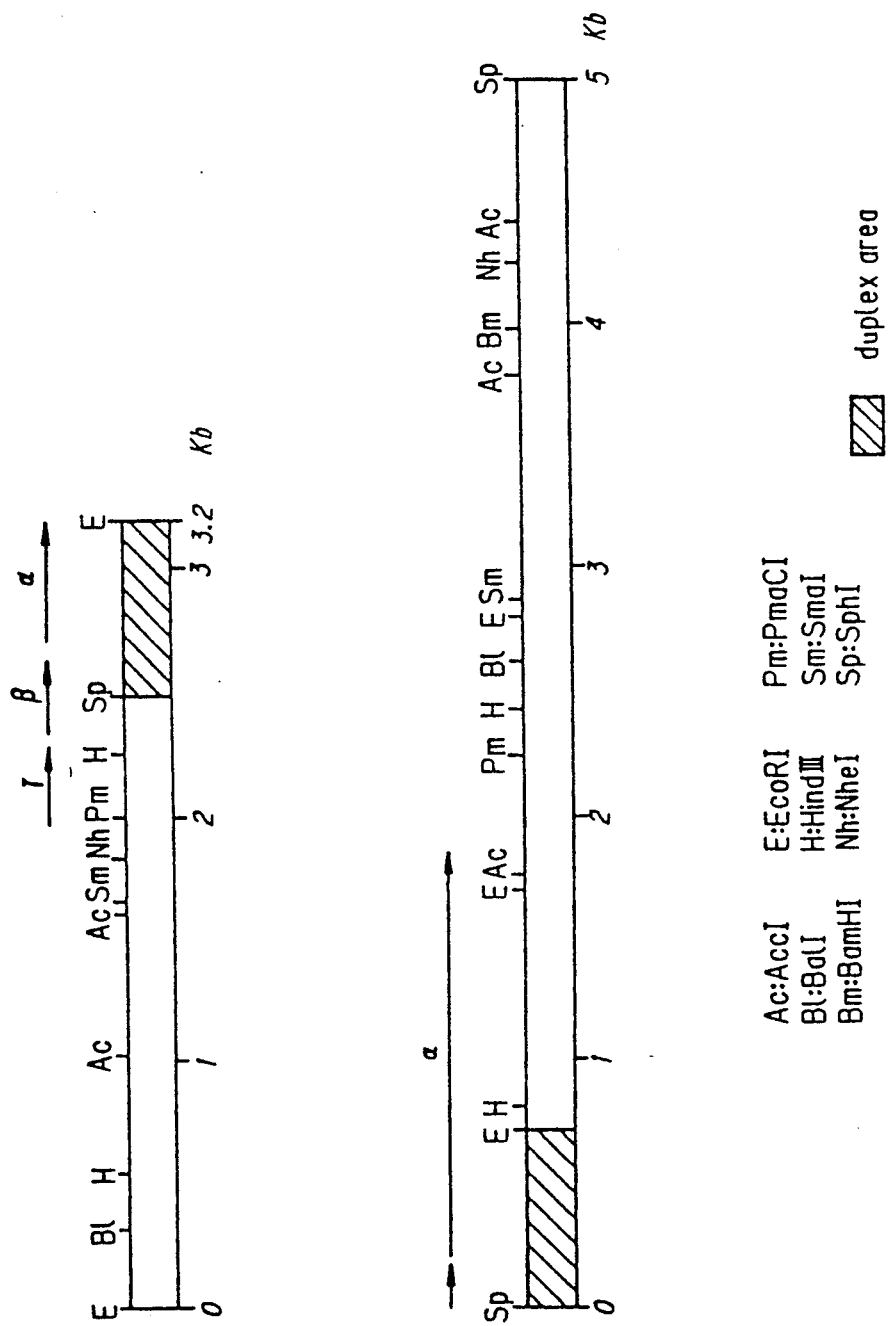
FIG. 1 shows a part of the restriction enzyme map of plasmid pUME and plasmid pUMS.

Under the circumstances, the present inventors made intensive studies on the process for producing the highly stable urease derived from Bacillus sp. TB-90 (FERM BP-795) by utilizing the techniques of genetic engineering, and succeeded in cloning the structural gene of said urease derived from Bacillus sp. TB-90 (FERM BP-795) and in its expression. This invention was accomplished on the basis of these findings.

Thus, this invention provides the structural gene of urease derived from Bacillus sp. TB-90 (FERM BP-795), a recombinant DNA capable of replicating in *Escherichia coli* carrying a vector into which said structural gene has been introduced, and a process for producing the urease, which comprises cultivating *Escherichia coli* carrying said recombinant DNA and isolating the urease from the culture mixture.

In the descriptions and drawings of this specification, peptides and amino acids are represented by the abbreviations adopted in IUPAC or commonly employed in this field, and the same applies to the expression of base sequences in DNA and of nucleic acids.

The structural gene of urease of this invention can be obtained as explained below by referring, for example, to the method described in "Molecular Cloning, 2nd edition" published from Cold Spring Harbor Laboratory in 1989.

(1) Urease was produced by using Bacillus sp. TB-90 (FERM BP-795) according to the method described in Japanese Patent Kokai No. 175174/1987, the crude product was then purified by chromatography (such as ion-exchange chromatography and gel filtration), the purified product thus obtained was subjected to amino acid analysis to acquire the amino-acid sequence information, and synthetic DNA probe was prepared based on the information thus obtained.

(2) Separately, Bacillus sp. TB-90 strain (FERM BP-795) was cultivated, and the whole chromosomal DNA was extracted by the usual method.

(3) The whole chromosomal DNA obtained in Step (2) above was digested by the use of a proper restriction enzyme to give fragments of the chromosomal DNA.

(4) The chromosomal DNA fragments thus obtained were subjected to electrophoresis on agarose gel, followed by Southern hybridization with the synthetic DNA probe obtained in Step (1) above, thus analyzing the hybridization sites between said DNA fragments and the synthetic DNA probe.

(5) The chromosomal DNA fragments obtained in the same way as Steps (2) and (3) above were subjected to electrophoresis on agarose gel, and the portion correspoding to the analytical result obtained in Step (4) above was cut out from the agarose gel, thus giving the chromosomal DNA fragment that will hybridize with the synthetic DNA probe.

(6) A vector plasmid was digested with the same restriction enzyme as used for digestion of the chromosomal DNA in Step (3) above, treated with alkaline phosphatase, and subjected to electrophoresis on agarose, followed by recovery of the open-chain plasmid having the same molecular weight as that of said vector plasmid.

(7) The chromosomal DNA fragment obtained in Step (5) above was linked to the open-chain plasmid obtained in Step (6) above by the use of a ligase to form a new plasmid.

(8) *Escherichia coli* cells were made to competent cells by the usual method, which were then transformed by the plasmid obtained in Step (7) above.

(9) The transformant thus obtained was subjected to primary screening based on a marker (such as a drug-resistant marker for vector plasmid), followed by colony hybridization using the synthetic DNA probe obtained in Step (1) above, thus giving a positive transformant.

(10) A plasmid DNA was obtained from the transformant obtained in Step (9) above by the usual method.

It is possible to determine the partial base sequence of the plasmid DNA thus obtained by the dideoxy chain termination method and to determine the structural gene.

The urease structural gene derived from Bacillus sp. TB-90 strain thus determined may be, for example, a DNA containing the base sequences encoding subunit amino-acid sequences (α, β, γ) as shown in the Sequence Listing by SEQ ID NO:1, SEQ ID NO:2 and SEQ ID NO:3.

As the vector plasmid for *Escherichia coli*, should be used the one which is capable of replicating in *Escherichia coli*, and many types are known and commercially available as such plasmids. In this invention, may be used any one of such known plasmids (e.g., pUC18, pUC19 and pBR322).

By the use of the structural gene of urease of this invention thus obtained, highly stable urease can be produced in large amounts by utilizing the recombinant DNA techniques.

Thus, urease of high stability can be produced according to the known recombinant DNA techniques, except for the use of the specific structural gene of urease as described above.

In more detail, one may prepare a recombinant DNA which will allow the urease gene of this invention to express itself in a host cell, introduce it into said host cell to effect transformation, and cultivate the transformant thus obtained.

As the host cell, may be used both of eukaryotic and procaryotic cells, and *Escherichia coli* is a typical example.

*Escherichia coli* can be cultivated by the known methods. For example, it may be cultivated in a medium containing suitable carbon and nitrogen sources and trace nutrients (such as vitamins). Both solid and liquid culture may be used, but culture with aeration and agitation is the most suitable for industrial purpose.

The speed of urease formation varies depending on the conditions adopted; hence, the urease is isolated when its amount formed reaches the maximum level.

The present inventors further studied to develop a more efficient process for producing said urease, and discovered that the open-reading-frame DNA contained in the urease operon of Bacillus sp. TB-90 is effective in obtaining active urease.

The use of an expression vector comprising three open-reading-frame DNA sequences encoding the amino-acid sequences represented by SEQ ID NO:4, SEQ ID NO:5 and SEQ ID NO:6 in the Sequence Listing showed several times higher efficiency compared with the conventional production by Bacillus sp. TB-90 strain (4.2 U/ml by cultivation at 52° C. for 16 hours).

In addition, the use of an expression vector further comprising one open-reading-frame DNA sequence that encodes the amino-acid sequence represented by SEQ ID NO:7 in the Sequence Listing showed ten-odd times higher efficiency compared with the conventional production by Bacillus sp. TB-90 strain.

Urease thus formed may be recovered by combination of known methods; for example, the cultured cells are collected by centrifugation, and then disrupted or dissovled, and purified urease is obtained by combination of ion-exchange chromatography, gel filtration and other steps.

According to this invention, the structural gene of highly stable urease derived from Bacillus sp. TB-90 can be obtained, and said urease can be efficiently produced by the techniques of genetic engineering.

The following examples will further illustrate the invention but are not intended to limit its scope.

REFERENCE EXAMPLE 1

Subunit Structural Analysis for Urease of Bacillus Sp. TB-90 (FERM BP-795), and Purification of Each Subunit Bacillus sp. TB-90 (FERM BP-795) was cultivated and the urease thus formed was collected and purified according to the method described in Japanese Patent Kokai No.175174/1987. Analysis of this purified enzyme by SDS-PAGE showed three bands corresponding to molecular weights of 66K, 12K and 8K, indicating its heterogeneous subunit structure. These subunits were named α, β and γ in descending order of molecular weight.

Purification of each subunit was performed as described below. About 2 mg of enzyme sample was dissolved in 0.5 ml of 100 mM Tris-HCl buffer solution containing 2% SDS and 50 mM β-mercaptoethanol (pH 8.5), the solution was boiled for ten minutes to effect denaturation, 50 μl aqueous solution of sodium monoiodoacetate (10 mg/ml) was added, and the mixture was allowed to stand at room temperature for 30 minutes while shielding light, thereby carboxymethylating cystein. α-Subunit, β-subunit and γ-subunit were then separated by using an HPLC gel filtration column (TSK G3000SW; product of Tosoh Co., Ltd.), with 125 mM Tris-HCl buffer solution containing 0.1% SDS and 1 mM EDTA (pH 6.8) being flown at a speed of 0.5 ml/min. The fraction containing the three subunits thus obtained was treated by the use of C8 reverse-phase column for HPLC (FP-308-125I; product of Tosoh Co., Ltd.) (gradient elution with solutions containing 0.1% TFA and 0–60% acetonitrile).

REFERENCE EXAMPLE 2

Determination of Amino Acid Sequence at N-terminal of Each Subunit, and Preparation of Synthetic DNA The amino-acid sequence at N-terminal of each subunit was determined by using Protein Sequencer 477A (product of Applied Biosystems Inc.). The result is shown below.

α-Subunit: SEQ. ID NO: 9:
N—XFXMXXK<u>EYADMFGP</u>TVGDAIXLA

β-Subunit: SEQ. ID NO: 10:
N—MIPGEYVL<u>KKEPIL</u>XNXN

γ-Subunit: SEQ. ID NO: 11:
N—MXLTSX<u>EMEKLAMI</u>VVAAXLA

Three synthetic DNAs were prepared by using a DNA synthesizer (Model 380B; product of Applied Eiosystem Inc.) based on the underlined portions in the above aminoacid sequences (portions of high specificity on transformation to DNA base sequences). After treatment at 65° C. for 12 hours, the reaction mixture was concentrated to about 100 μl by the use of a rotary evaporator, 10 μl of 3M sodium acetate solution (pH 4.8) and 250 μl ethanol were added to the concentrate, and the resulting mixture was allowed to stand at −80° C. for 30 minutes and then subjected to centrifugal separation for ten minutes (0° C., 15000 rpm), affording purified synthetic DNA as precipitate.

EXAMPLE 1

Southern Hybridization a) Preparation of probes

Each of the synthetic DNAs prepared and purified in Reference Example 2 was treated with T4 DNA kinase by heating in a reactive solution (containing 50 mM Tris-HCl buffer solution (pH 7.6), 10 mM MgCl$_2$, 10 mM 2-mercaptoethanol and 100 μM [γ-$^{32}$P]ATP) at 37° C. for 30 minutes, and the 5'-terminal of the product was labeled, thus giving α-probe, β-probe and γ-probe as shown below.

α-Probe (SEQ. ID No: 12): 5' GAR TAY GCN GAY ATG TTY GG 3'
(20 mer 64 species)
β-Probe (SEQ. ID NO: 13): 5' AAR AAR GAR CCN ATN YT 3'
(17 mer 256 species)
Y-Probe (SEQ. ID NO: 14): 5' GAR ATG GAR AAR YTN ATG AT 3'
(20 mer 64 species)
(wherin N = A, C, G, T; R = A, G; Y = C, T)

b) Purification of the whole chromosomal DNA of Bacillus sp. TB-90 strain

Bacillus sp. TB-90 strain was subjected to shaking culture at 52° C. overnight in 10 ml of P medium (containing 0.1% glucose, 0.3% yeast extract, 0.3% peptone, 0.1% K$_2$HPO$_4$, 0.05% KH$_2$PO$_4$ and 0.05% MgSO$_4$.7H$_2$O), and the culture solution was inoculated at 1% concentration onto 1 liter of C medium (containing 0.2% urea, 1.0% glucose, 0.1% K$_2$HPO$_4$, 0.1% trace salt solution, 0.05% yeast extract, 0.05% peptone and 0.05% MgSO$_4$.7H$_2$O; wherein the trace salt solution contained 2.5 g MgSO$_4$.7H$_2$O, 0.5 g FeSO$_4$.7H$_2$O, 0.5 g CaCl$_2$.2H$_2$O, 0.06 g CoCl$_2$.2H$_2$O, 0.5 g CuSO$_4$.7H$_2$O, 1.7 g MnSO$_4$.7H$_2$O, 0.6 g NaCl, 0.06 g ZnSO$_4$.7H$_2$O, 1.0 g KCl and 2.38 g NiCl$_2$.6H$_2$O per liter). Cultivation was continued at 50° C. for 16 hours by using a 5 ml conical flask and a rotary shaker, and the grown cells were collected by centrifugation for five minutes (0° C., 7000 rpm). The cells thus obtained were washed with 40 ml of TES buffer solution (containing 20 mM Tris-HCl buffer solution (pH 8.0), 5 mM EDTA and 100 mM sodium chloride) and then suspended in 30 ml of a buffer solution containing 50 mM Tris-HCl and 20 mM EDTA (pH 3.0), lysozyme was added to this suspension to a concentration of 1 mg/l, and the resulting mixture was mildly stirred at 37° C. for 30 minutes. One milliliter of 10% SDS solution was then added, the mixture was incubated at 70° C. for 60 minutes, 30 ml of phenol saturated with TE (containing 10 mM Tris and 1 mM EDTA; pH 8.0) was further added, and the mixture was mildly stirred. Centrifugal separation was continued for 20 minutes at 12000 rpm to collect the upper aqueous layer, this operation was performed once again, the aqueous solutions thus collected were combined together, the same volume of cooled ethanol was added to the combined solution, and the DNA which separated out was collected and dehydrated by being dipped in 70%, 80% and 90% ethanol, successively. The dried DNA thus obtained was dissolved in 15 ml TE, 0.5 ml of RNase solution (containing 1 mg/ml RNase A and 2 mg RNase T1) was added, and the resulting mixture was incubated at 37° C. for 30 minutes. Phenol saturated with TE (5 ml) was added, the mixture was mildly stirred, and centrifuged for 20 mintues at 8000 rpm and the upper aqueous layer was collected. This procedure of chloroform-butanol-isoamyl alcohol extraction was repeated seven times. To the aqueous solution, was added 5 ml of a solvent mixture (containing 24 parts of chloroform, 25 parts of n-butanol and 1 part of isoamyl alcohol, by volume), the resulting solution was stirred mildly, and centrifuged for one minute at 1000 rpm. The upper aqueous layer was collected. This procedure of phenol extraction was repeated five times and the aqueous solution was dialyzed against TE at 4° C. over a period of 24 hours, thereby affording the whole chromosomal DNA of said sp. TB-90 strain.

c) Hybridization

To 10 μg of the DNA obtained above was added 30 units of EcoRI, and the mixture was incubated at 37° C. for three hours, thereby completely digesting the DNA. The solution thus obtained containing digested DNA was subjected to electrophoresis on 1% agarose gel, and Southern hybridization was performed according to the method described on p. 9.34 to 9.58 in "Molecular Cloning, 2nd edition" published from Cold Spring Harbor Laboratory in 1989. The actual conditions herein adopted are as described below. Using 6×SSC (standard SSC contains 150 mM sodium chloride and 15 mM trisodium citrate), 0.1% SDS, 0.2% BSA, 0.2% Ficoll and 0.2% PVP, hybridization was carried out for 12 hours at 50° C. for α-probe, at 38° C. for β-probe and at 46° C. for γ-probe. Washing was carried out for 30 minutes in 6×SSC and 0.1% SDS at 54° C. for γ-probe, at 46° C. for β-probe and at 52° C. for γ-probe, and autoradiography was used for analysis. It was demonstrated that all the probes had hybridized with a 3.2-kb fragment.

EXAMPLE 2

Cloning of EcoRI Fragment of 3.2 kb

The whole DNA of TB-90 strain obtained above (5 μg) was digested by 15 units of EcoRI, the reaction mixture was subjected to electrophoresis on agarose gel, and the fragment in the vicinity of 3.2 kb was cut out from the gel by using a razor. To the fragment thus obtained, was added 8M aqueous solution of sodium perchlorate in an amount three times as much, the mixture was treated at 37° C. for two minutes, DNA was adsorbed on a glass filter of 6 mmφ (product of Whatman Co.), and the glass filter was washed with 1 ml of TE containing 6M sodium perchlorate and with 1 ml of 95% ethanol in that order. After drying, 30 μl TE was added, and the mixture was treated at 37° C. for 30 minutes, followed by centrifugal separation for two minutes (room temperature, 15000 rpm), thus recovering DNA (Sample A). Separately, a mixture of vector plasmid pUC19 (0.1 μg) and EcoRI (five units) was incubated at 37° C. for two hours, 1/5 volume of 1M Tris-HCl buffer solution (pH 9.0) and 0.5 unit of alkaline phosphatase were then added, the reaction was carried out at 65° C. for 30 minutes, the reaction mixture was subjected to electrophoresis on agarose gel, and the band corresponding to the molecular weight of pUC19 was recovered in the same way as above (Sample B).

Sample A and Sample B were mixed together, 300 units of T4 DNA ligase was then added, and the mixture was heated in a reactive solution (containing 66 mM Tris-HCl (pH 7.6), 6.6 mM magnesium chloride, 10 mM DTT and 0.1 mM ATP) at 4° C. for 12 hours to link Sample A with Sample B (Sample C).

Transformation of E. coli HB101 strain was performed by creating competent cells according to the method described on p. 1.82 to 1.84 in "Molecular Cloning, 2nd edition" published from Cold Spring Harbor Laboratory in 1989, and using the linked product (Sample C) obtained above. The transformants were selected on LB medium (1% yeast extract, 0.5% trypton and 0.5% NaCl; product of Difco Laboratories) further containing 50 μg/ml ampicillin and 1.5% agar and transferred to a nitrocellulose filter, and colony hybridization was performed using γ-probe (the most specific one among the three probes obtained above) according to the method described on p. 1.90 to 1.104 in "Molecular Cloning, 2nd edition" published from Cold Spring Harbor Laboratory in 1989. As a result, nine positive clones among about 500 transformants were obtained. From these transformants, was prepared plasmid DNA by the method described on p. 1.25 to 1.28 in "Molecular Cloning, 2nd edition" published from Cold Spring Harbor Laboratory in 1989. The plasmid DNA thus obtained was cleaved by the use of a restriction enzyme that cleaves pUC 19 vector only at the multicloning site. The result was that six clones among the above-described nine positive clones show the same restriction-enzyme pattern and that the residual three clones also show the same pattern, and the former was named pUME01 and the latter was named pUME10. Southern hybridization was then performed by using the three probes described above, demonstrating that all of the three probes hybridized with pUME01 and pUME10, and showing the hybridized portion of each probe on the cloned gene. It was also demonstrated that the inserted fragment was the same with pUME01 and pUME10 except for the insertion direction to the vector. The restriction enzyme map of the cloned DNA fragment of 3.2 kb is shown in a raised portion of FIG. 1.

EXAMPLE 3

Determination of Partial Base Sequence, and Gene Walkig a) Determination of partial base sequence The base sequence in the portion in which each probe had hybridized was determined by the dideoxy chain termination method [Sanger, F. S., et al.; Proc. Natl. Acad. Sci. U.S.A., 74, 5463 (1977)].

γ-Probe had hybridized with the SmaI-HindIII fragment, β-probe with the HindIII-SphI fragment and α-probe with the SphI-EcoRI fragment; hence, these fragments were subcloned to pUC118 and pUC119 to transform Escherichia coli MV1184 strain. From this transformant carrying these plasmids, was prepared single-stranded DNA according to the method described on p.4.48 in "Molecular Cloning, 2nd edition (1989)", and its base sequence was determined by using DNA Sequence Kit (product of Takara Shuzo Co., Ltd). As a result, it was found that the base sequence expected from the N-terminal amino-acid sequence in each of γ-, β- and α-subunits is contained therein, indicating that the cloned gene fragment contains the objective gene and suggesting that the subunit genes are arranged in that order from 5'-terminal side, thus forming an operon structure. However, because this gene fragment does not contain the total length presumable from the molecular weight of α-subunit, the fragment containing the total length of α-subunit structural gene was obtained by Gene Walking as explained below.

b) Gene Walking

In order to isolate a fragment positioned downstream of the 3.2 kb gene fragment obtained above, the whole DNA of TB-90 strain was digested by HindIII, SmaI, SphI, NheI, PmaCI, BamHI and PstI (restriction enzymes suited for obtaining the objective gene fragment), and each of the digested products was subjected to Southern hybridization by using, as the probe, the SphI-EcoRI fragment coding α-subunit, thereby forming hybrids of 0.9 kb, 3.7 kb, 5.0 kb, 5.0 kb, 2.7 kb, 11 kb and 20 kb, respectively. Prehybridization was carried out at 42° C. for four hours by using 50% formamide, 5×SSC, 50 mM sodium phosphate buffer solution (pH 7.0), Denhardt solution of ten time higher concentration (standard Denhardt solution contains 0.02% BSA, 0.02% Ficoll 400 and 0.02% PVP) and 1% SDS. Final hybridization was performed at 42° C. for 12 hours by using a mixture of 50% formamide, SSC of five times higher concentration, 50 mM sodium phosphate buffer solution (pH 7.0), Denhardt solution of five times higher concentration and 0.5% SDS, further containing a $^{32}$P-labeled probe prepared from the above DNA fragment by the use of Random-Primed DNA Labeling Kit (product of Boehringer Mannheim Co.) and denatured by heating at 100° C. for ten minutes. Washing was carried out five times at room temperature in 2×SSC and 0.1% SDS, and then two times at 65° C. in SS of 1/10 concentration and 0.1% SDS. The SphI fragment of 5 kb, which is considered to be the most suitable among the hybridized bands, was cloned in the same way as in Example 2 and named pUMS. The restriction enzyme map of the DNA fragment thus obtained is shown in a lower portion of FIG. 1.

COMPARATIVE EXAMPLE 1

Figure 2:
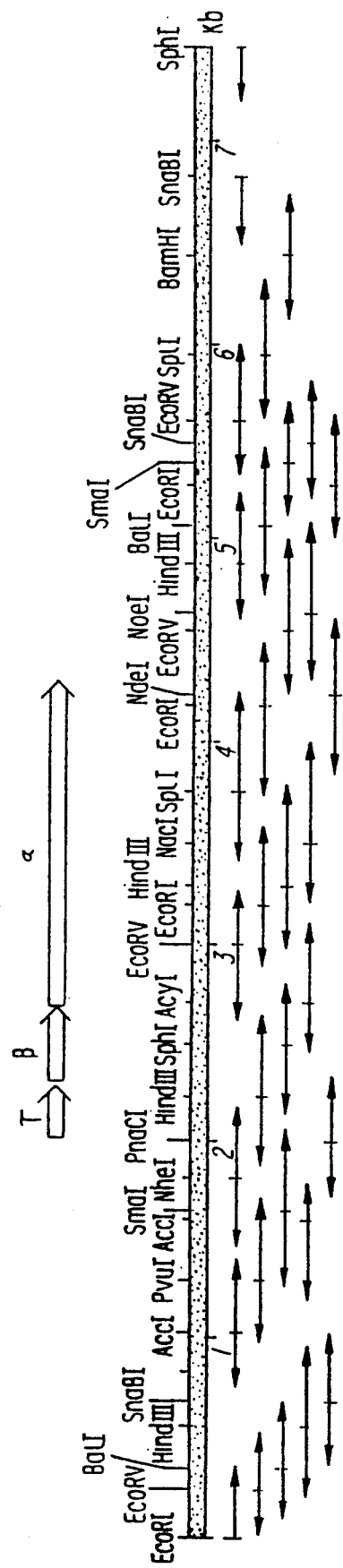
FIG. 2 shows the sequence strategy of the gene.

Determination of Base Sequence of Urease Gene and Its Peripheral Portion, and Comparison with Urease of Jack Bean and Those Derived from Other Bacteria The total length of the gene obtained above is 7.5 kb for EcoRI-SphI, and the base sequence was determined with the portion of 6.5 kb for EcoRI-BamHI. Its sequence strategy is shown in FIG. 2, and the base sequence in SmaI fragment is shown 3.7 kb. The method of determination is the same as in Example 3.

Comparison of the amino-acid sequence of γ-, β- and α-subunits deduced from the base sequence of the urease gene of TB-90 strain with the amino-acid sequence of the jack bean urease showed the following homology: γ-subunit 60%, β-subunit 56%, and α-subunit 67%. The base sequence in the urease gene of Proteus mirabilis was recently reported. Since the structure of this gene is similar to that of the urease gene of TB-90 strain, the amino-acid sequence of the porteins coded by this gene and corresponding to γ-, β- and α-subunits was also compared, showing the following homology (γ-subunit 61.6%, β-subunit 49.5%, and α-subunit 68.9%).

EXAMPLE 4

Expression of Urease Gene in *Escherichia coli* a) Gene reconstitution, and detection of its activity expressed in *Escherichia coli*

Urease gene was reconstituted by linking SphI fragment of 5.0 kb with EcoRI fragment of 3.2 kb obtained above.

In the first place, EcoRI-SphI fragment of 2.5 kb was obtained from pUME01 by the method described in Example 2, SphI-BamHI fragment of 4.0 kb was obtained from pUMS in the same way, and fragments were obtained from pUC18 and pBR322 by repeated digestion with EcoRI and BamHI. The fragments thus obtained were mixed together, the mixture was subjected to ligation reaction, and the reaction mixture was used for transformation of *Escherichia coli* HB101 strain. The plasmids thus obtained were named pUM01 (vector: pUC18) and pUBM01 (vector: pBR322).

In addition, the fragment obtained by digesting pUM01 with SmaI was subcloned at the SmaI site of pUC19, and the product in the same direction of lac promotor was named pUM02 and that in the opposite direction was named pUM20. Similarly, the gene fragment obtained by digesting pUM01 with NheI and BamHI was subcloned at the XbaI and BamHI site of pUC19, and the product was name pUM03. Furthermore, several kinds of plasmids for different genes were constituted, which are also shown in FIG. 6 together with the above plasmids. In the names of plasmids, pU—shows insertion into pUC vector and pT—shows insertion into pTTQ vector.

Expression of the urease gene in *Escherichia coli* was first effected by using *E. coli* HB101 strain (carrying pUM01, pUM02 and pUM03) and MV184 strain (carrying lacI$^q$ gene) Each of these strains was cultivated overnight at 37° C. in LB medium containing 0.5% glucose and 50 μg/ml ampicillin, the culture solution was then inoculated to fresh LB medium containing 50 μl/mg ampicillin at a concentration of 1%, IPTG (isopropyl-β-D-thiogalactopyranoside) was added to a concentration of 1 mM when $OD_{660}$ reached 0.6, and cultivation was further continued for three hours. The grown cells were collected, washed with 10 mM potassium phosphate buffer solution (pH 6.8), and suspended in potassium phosphate buffer solution containing 0.1% Triton X-100 and 2 mM EDTA (pH 6.8). The suspension thus obtained was treated with Cell Disrupter 200 (product of Branson Co.) to disrupt the cells by ultrasonic waves, and the supernant obtained by centrifugation was tested for urease activity, but no activity was detected at all. Activity was measured by the method using Phenol red (a simple method) for qualitative analysis and by the Coupled enzyme method (a high accuracy method) for quantitative analysis. These two methods are explained below.

[1] Activity measurement by the simple method
1) Principle
Formation of ammonia caused by urea decomposition by urease causes increase in pH
2) Reagents used
A. 20 mM Tris-HCl (pH 6.9), Phenol red 24.0 mg/100 ml
B. A 5 ml, $H_2O$ 95 ml, urea 1.2 g (pH becomes 6.8)
3) Measurement procedure
Sample (0.05 ml) is mixed with Reagent B, the mixture is incubated at 37° C. for 10 to 20 minutes, and values of OD at 560 nm were measured with the passage of time or at the end of incubation.

[2] High-accuracy measurement
1) Principle

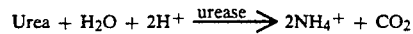

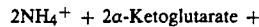

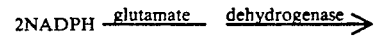

$$2Glutamate + 2H_2O + 2NADP^+$$

The amount of NADPH consumed is measured by the change in absorbance at 340 nm.

2) Definition
The enzyme activity forming two micromoles of ammonia (by decomposition of one micromole of urea) in one minute under the conditions described below is defined as one unit (U).

3) Reagents used
A. 6.0M aqueous solution of urea [36 g urea is dissolved in distilled water to make up 100 ml.] (to be prepared before use)
B. 50 mM Tris-HCl buffer solution (pH 8.0)
C. 0.25M Aqueous solution of α-ketoglutaric acid [α-Ketoglutaric acid (730 mg) is dissolved in about 15 ml distilled water, 5N-NaOH is added to adjust pH to 5.0±0.1, and distilled water is added to make up 20 ml.] (to be prepared before use)
D. 15 mM Aqueous solution of NADPH [136 mg NADPH-$Na_4.4H_2O$ is dissolved in 10 ml distilled water.] (to be prepared before use).
E. Reagent mixture (to be prepared immediately before use and stored under ice cooling)
69 ml Tris-HCl buffer solution (B)
0.3 ml Aqueous solution of α-ketoglutaric acid (C)
1.8 ml Aqueous solution of NADPH (D)
0.9 ml Distilled water
F. Solution of glutamate dehydrogenase (GlDH) [Tris-HCl buffer solution (GlDH of Toyobo Co., Ltd. containing no ammonia is suitable for the purpose of this invention) is diluted with distilled water to a concentration of about 1,000 U/ml.]
Enzyme solution: Enzyme sample is dissolved in 10 mM potassium phosphate buffer solution containing 2 mM EDTA (pH 7.0; previously ice-cooled), and the solution is diluted with the same buffer solution as above to a concentration of 0.07 to 0.25 U/ml and stored under ice cooling.

4) Procedure
(1) The following reactive solution mixture is previously heated at 37° C. for five minutes.
2.4 ml Reagent mixture (E)
0.05 ml GlDH solution (F)
0.35 ml Distilled water
0.10 ml Enzyme solution
(2) 0.10 ml of substrate solution (A) is added, the mixture is mildly stirred, and the changes in absorbance at 340 nm were recroded for three to four minutes by the use of a spectrophotometer set at 37° C. with water as control, thus obtaining the change per minute from the initial linear portion (ΔODtest).
(3) A blank test is conducted by adding, to the reactive solution mixture (1), 0.1 ml of a diluted enzyme soluiton (10 mM potassium phosphate buffer solution containing 2 mM EDTA; pH 7.0), and the same operations as above are performed, thereby obtaining the change in absorbance per minute (ΔODblank).

5) Calculation formulas $$U/ml = \frac{\Delta OD/\min[(\Delta OD\text{test}) - (\Delta OD\text{blank})] \times 3.0 \text{ (ml)} \times \text{Dilution Factor}}{6.22 \times 2 \times 1.0 \times 0.10 \text{ (ml)}}$$

$$= \Delta OD/\min \times 2.41 \times \text{Dilution Factor}$$

$$U/mg = U/ml \times 1/C$$

6.22: Millimolar absorptivity coefficient of NADPH ($cm^2$/micromole)
2: A coefficient based on the fact that hydrolysis of one mole urea causes oxidation of two moles NADPH
1.0: Optical path length (cm)
C: Enzyme concentration in its solution prepared (mg/ml)

b) Expression of urease activity when using a medium containing only urea as the nitrogen source (R medium)

In order to study the possibility of urease activity expression depending on medium conditions, the activity was measured by using R containing medium with only urea as the nitrogen source (having a composition as shown below).

R medium is based on M9 salts not containing ammonium chloride, which further contains 0.5% of glycerol, sodium succinate or glucose as carbon source; 30 mM of deionized urea; 0.1% of a trace salt solution; amino acids (20 μg/ml of proline and leucine for HB101 strain, or the same amount of proline for MV1184 strain); 5 μg/ml of thiamin; and 100 μg/ml of ampicillin. IPTG was used at a concentration of 0.05 mM or 0.5 mM.

Precultivation was carried out in LB medium (containing 0.5% glucose and 100 μg/ml ampicillin) at 37° C. overnight, and the grown cells were collected by centrifugation, washed with 150 mM NaCl solution, and inoculated to RA medium (a medium similar to R medium, in which 10 mM ammonium sulfate is used in place of urea) to perform adaptation for 24 hours. The culture bloth was then inoculated to 15 ml of R medium containing urea, shaking cultivation was carried out at 37° C. for 36 hours, growth curve during cultivation was recorded, and the activity of grown cells was measured. The strains used are E. coli MV1184 carrying pUC19, pUM01, pUM02 and pUM03. The results obtained are summarized in Table 1.

TABLE 1

Growth and Urease Activity of E. coli MV184 Carrying a Variety of Plasmids

| C-Source | Succinate | | | Glucose | | |
|---|---|---|---|---|---|---|
| IPTG(mM) | 0 | 0.05 | 0.5 | 0 | 0.05 | 0.5 |
| pUM01 | — | ± | ± | — | ± | + |
| pUM02 | + | + | + | ± | +++ | + |
| pUM03 | ++ | — | — | + | ++ | ± |

—: No significant growth observed
±: Growth in some degree but low activity
+: Satisfactory growth and activity
++, +++: Satisfactory growth with high activity Significant difference in growth was observed about 15 to 21 hours after inoculation. The strain carrying vector pUC19 showed no growth even after 36 hours. The above experimental results were of high reproducibility, except that the data of mark "—" in the table showed somewhat better growth in some cases.

c) Examination of urease activity expressed in Escherichia coli, in different media Because the results obtained above suggest that expression of urease activity depends on the conditions of media, it was attempted to perform activity expression by using media which are intermediate between LB medium and the above restriction medium. As the preliminary test, activity was measured for E. coli MV1184 by using media, prepared by diluting LB medium with M9 (containing no ammonium chloride), which contain 50%, 30%, 20%, 10% or 5% LB; 0.5% of sodium succinate; 100 μl/ml of amplicillin; and 1% of trace salt solution. The result was that the highest activity was observed with the medium containing 10% of LB; hence, it was decided to use this medium in the subsequent experiments.

This medium is named ND medium (Nitrogen Deficient medium), and the medium prepared by adding urea to ND medium to a concentration of 30 mM is named NDU medium. The following experiments were carried out to examine the effect of urea on activity expression and the relationship between IPTG induction and gene fragments.

Preliminary cultivation
↓ LB, 30° C., overnight
Washing with 150 mM NaCl solution, and 1% inoculation
↓
Final cultivation 15 ml ND or NDU, 37° C., 18 hours
↓
Cell collection by centrifugation
↓
Washing with 10 mM K phosphate buffer (pH 6.8)
↓
Suspension in 1 ml of 10 mM K phosphate buffer (pH 6.8) containing 2 mM EDTA and 0.1% Triton X-100
↓
Ultrasonic distruption (pulse, 1 minute) 0° C.
↓
Centrifugation (15000 rpm, 15 minutes) and collection of supernatant
↓
Measurement of activity and amount of protein The amount of protein was measured by the Lowry's method [O. H. Lowry, N. J. Rosebrough, A. L. Farr, R. J. Randall, J. Biol. Chem., 193, 265 (1951)].
Activity was herein measured at pH 7.5
The results obtained are summarized in Table 2.

TABLE 2

Activity of E. coli Carrying a Variety of Plasmids in ND and NDU Media

| | 0 | | | 0.1 | | | 1 | | |
|---|---|---|---|---|---|---|---|---|---|
| IPTG (mM) | U/ml | mg/ml | U/mg | U/ml | mg/ml | U/mg | U/ml | mg/ml | U/mg |
| | ND Medium | | | | | | | | |
| MV1184 | | | | | | | | | |
| pUM01 | 0.215 | 0.234 | 0.919 | — | — | — | 0.233 | 0.240 | 0.971 |
| pUM02 | 0.246 | 0.266 | 0.925 | — | — | — | 0.169 | 0.228 | 0.741 |

TABLE 2-continued

Activity of E. coli Carrying a Variety of Plasmids in ND and NDU Media

| IPTG (mM) | 0 | | | 0.1 | | | 1 | | |
|---|---|---|---|---|---|---|---|---|---|
| | U/ml | mg/ml | U/mg | U/ml | mg/ml | U/mg | U/ml | mg/ml | U/mg |
| pUM03 | 0.240 | 0.233 | 1.03 | 0.246 | 0.233 | 1.06 | 0.231 | 0.230 | 1.00 |
| HB101 | | | | | | | | | |
| pUM01 | 0.028 | 0.250 | 0.112 | 0.025 | 0.245 | 0.102 | 0.021 | 0.243 | 0.086 |
| pUBM01 | 0 | 0.265 | 0 | 0.024 | 0.253 | 0.095 | 0.034 | 0.241 | 0/141 |
| pTBL | 0 | 0.194 | 0 | 0.051 | 0.246 | 0.207 | 0 | 0.193 | 0 |
| pTPA | 0.134 | 0.181 | 0.740 | 0.141 | 0.192 | 0.734 | 0.136 | 0.225 | 0.604 |
| NDU Medium | | | | | | | | | |
| MV1184 | | | | | | | | | |
| pUM01 | 0 | 0.263 | 0 | — | — | — | 0 | 0.259 | 0 |
| pUM02 | 0.032 | 0.313 | 0.102 | — | — | — | 0 | 0.255 | 0 |
| pUM03 | 0.068 | 0.266 | 0.256 | 0.053 | 0.280 | 0.189 | 0.044 | 0.276 | 0.159 |
| HB101 | | | | | | | | | |
| pUM01 | 0.021 | 0.265 | 0.079 | 0 | 0.303 | 0 | 0 | 0.253 | 0 |
| pUBM | 0 | 0.243 | 0 | 0 | 0.264 | 0 | 0 | 0.254 | 0 |
| pTBL | 0 | 0.226 | 0 | 0 | 0.234 | 0 | 0 | 0.230 | 0 |
| pTPA | 0.068 | 0.225 | 0.302 | 0.069 | 0.221 | 0.312 | 0.040 | 0.289 | 0.138 |

In the above table, U/ml represents activity per volume of culture solution, mg/ml represents the amount of protein per volume of culture solution, and U/mg represents specific activity per milligram of protein.

The above results suggest influence of nitrogen source in the activity expression; hence, E. coli MV1184 carrying pUM03, which causes best activity expresion, was cultivated in the following media and activity was measured.

(1) M9
(2) M9+0.2% casamino acids
(3) MC
(4) M9 (containing no ammonium chloride)+20 µg/ml glutamic acid
(5) M9 (containing no ammonium chloride)+20 µg/ml arginine
(M9 contains 0.5% sodium succinate as carbon source.)

Cells were grown well in (2) and (3), but were not grown so well in (1), (4) and (5). The activity per volume of culture solution was high in (3) and (4), and very low in (2). The activity per protein amount was extremely high in (4).

The activity per amount of total soluble protein was compared by using media (1) to (5) and ND media with varied LB composition. The result is shown below.

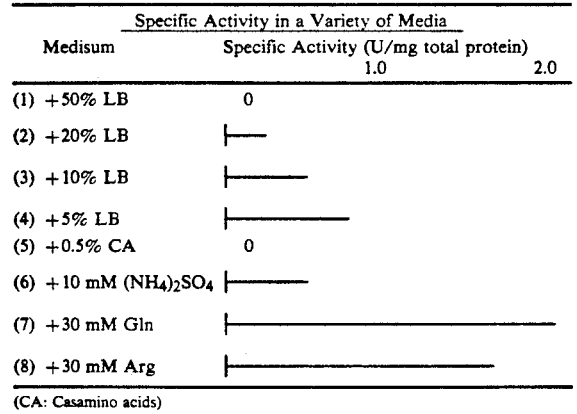

| Medisum | Specific Activity in a Variety of Media Specific Activity (U/mg total protein) |
|---|---|
| | 1.0    2.0 |
| (1) +50% LB | 0 |
| (2) +20% LB | |
| (3) +10% LB | |
| (4) +5% LB | |
| (5) +0.5% CA | 0 |
| (6) +10 mM (NH4)2SO4 | |
| (7) +30 mM Gln | |
| (8) +30 mM Arg | |

(CA: Casamino acids)

EXAMPLE 5

Efficient Expression of Urease (a) Gene reconstitution

NheI-SphI fragment of 750 bp was obtained from pUMS according to the method described in Example 2. Separately, the whole DNA of TB-90 strain was digested with HindIII, subjected to electrophoresis on agarose gel and then subjected to Southern hybridization by using the above. NphI-SphI fragment as probe to link the fragment of 6.4 kb. The HindIII fragment was recovered from gel, and liked to the HindIII site of pUC18, thus giving pUMH of 9.1 kb.

In addition, the fragment of 5.2 kb obtained by digestion of pUM01 with SphI, followed by electrophoresis on agarose gel, was linked to the fragment obtained by digestion of pUMS and electrophoresis on agarose gel, thus giving pUM00.

Figure 3:
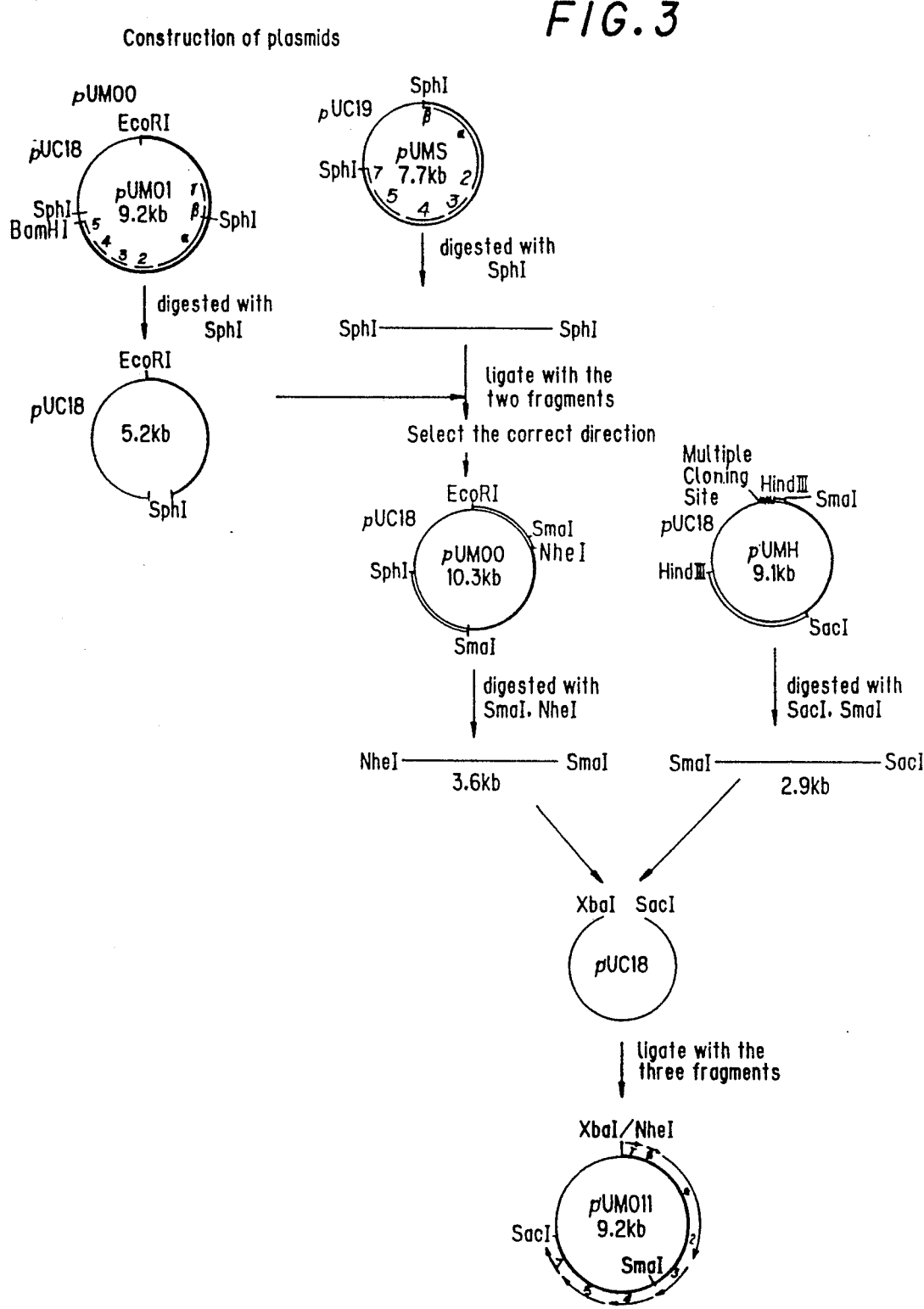
FIG. 3 shows a drawing for constructing expression plasmid pUMO11.

Furthermore, pUM011 was obtained by ligation of pUM00's NphI-SmaI fragment of 3.6 kb and pUMH's SmaI-SacI fragment of 2.9 kb to the XbaI and SacI site of pUC13, followed by subcloning. Its construction map is shown in FIG. 3. The SamI-BglII fragment of 6.1 kb is shown in SEQ ID:8 in the Sequence Listing.

(b) Expression

E. coli MV1184 was transformed by using pUM011 obtained above [Escherichia coli MV1184/pUM011 (FERM BP-3483)].

E. coli MV1184/pUM011 was cultivated in ND medium (M9 (free of ammonia)+10% LB+0.5% sodium succinate +1% trace metal salt solution+10 µM NiCl2) at 37° C. for 17 hours, the grown cells were disrupted by ultrasonication, the resulting solution was centrifuged, and the supernatant was collected. Its activity and protein content were 56.7 U/ml and 122 U/mg, respectively.

(c) Control test pUM011 obtained above was mutated at various restriction sites by frameshift using DNA polymerase Kienow fragment or linker insertion, and used for transformation of E. coli MV1184. The transformant thus obtained was cultivated under the same conditions as in Paragraph (b) above, and the activity and protein content of the supernatant were measured. The result is shown FIG. 4.

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
      ( A ) LENGTH: 99 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:1:

```
Lys Leu Thr Ser Arg Glu Met Glu Lys Leu Met Ile Val Val Ala Ala
 1               5                  10                  15
Asp Leu Ala Arg Arg Arg Lys Glu Arg Gly Leu Lys Leu Asn Tyr Pro
                20                  25                  30
Glu Ala Val Ala Met Ile Thr Tyr Glu Val Leu Glu Gly Ala Arg Asp
                35                  40                  45
Gly Lys Thr Val Ala Gln Leu Met Gln Tyr Gly Ala Thr Ile Leu Thr
        50                  55                  60
Lys Glu Asp Val Met Glu Gly Val Ala Glu Met Ile Pro Asp Ile Gln
65                  70                  75                  80
Ile Glu Ala Thr Phe Pro Asp Gly Thr Lys Leu Val Thr Val His Asp
                85                  90                  95
Pro Ile Arg
```

( 2 ) INFORMATION FOR SEQ ID NO:2:

( i ) SEQUENCE CHARACTERISTICS:
      ( A ) LENGTH: 106 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:2:

```
Ile Pro Gly Glu Tyr Val Leu Lys Lys Glu Pro Ile Leu Cys Asn Gln
 1               5                  10                  15
Asn Lys Gln Thr Ile Lys Ile Arg Val Leu Asn Arg Gly Asp Arg Pro
                20                  25                  30
Val Gln Val Gly Ser His Phe His Phe Phe Glu Val Asn Gln Ser Leu
                35                  40                  45
Gln Phe His Arg Glu Lys Ala Phe Gly Met Arg Leu Asn Ile Pro Ala
        50                  55                  60
Gly Thr Ala Val Arg Phe Glu Pro Gly Asp Ala Lys Glu Val Glu Ile
65                  70                  75                  80
Ile Pro Phe Ser Gly Glu Arg Lys Val Tyr Gly Leu Asn Asn Val Thr
                85                  90                  95
Asn Gly Ser Val Glu Met Gly Lys Arg Lys
                100                 105
```

( 2 ) INFORMATION FOR SEQ ID NO:3:

( i ) SEQUENCE CHARACTERISTICS:
      ( A ) LENGTH: 568 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:3:

```
Ser Phe Ser Met Ser Arg Lys Gln Tyr Ala Asp Met Phe Gly Pro Thr
 1               5                  10                 15
Val Gly Asp Ala Ile Arg Leu Ala Asp Ser Glu Leu Phe Ile Glu Ile
               20                  25                  30
Glu Lys Asp Tyr Thr Thr Tyr Gly Asp Glu Val Lys Phe Gly Gly Gly
           35                  40                  45
Lys Val Ile Arg Asp Gly Met Gly Gln His Pro Leu Ala Thr Ser Asp
 50                  55                  60
Glu Cys Val Asp Leu Val Leu Thr Asn Ala Ile Ile Val Asp Tyr Thr
 65                  70                  75                  80
Gly Ile Tyr Lys Ala Asp Ile Gly Ile Lys Asp Gly Met Ile Ala Ser
                85                  90                  95
Ile Gly Lys Ala Gly Asn Pro Leu Leu Met Asp Gly Val Asp Met Val
            100                 105                 110
Ile Gly Ala Ala Thr Glu Val Ile Ala Ala Glu Gly Met Ile Val Thr
            115                 120                 125
Ala Gly Gly Ile Asp Ala His Ile His Phe Ile Cys Pro Gln Gln Ile
130                 135                 140
Glu Thr Ala Leu Ala Ser Gly Val Thr Thr Met Ile Gly Gly Gly Thr
145                 150                 155                 160
Gly Pro Ala Thr Gly Thr Asn Ala Thr Thr Cys Thr Pro Gly Pro Trp
                165                 170                 175
Asn Ile His Arg Met Leu Gln Ala Ala Glu Glu Phe Pro Ile Asn Leu
                180                 185                 190
Gly Phe Leu Gly Lys Gly Asn Cys Ser Asp Glu Ala Pro Leu Lys Glu
            195                 200                 205
Gln Ile Glu Ala Gly Ala Val Gly Leu Lys Leu His Glu Asp Trp Gly
210                 215                 220
Ser Thr Ala Ala Ala Ile Asp Thr Cys Leu Lys Val Ala Asp Arg Tyr
225                 230                 235                 240
Asp Val Gln Val Ala Ile His Thr Asp Thr Leu Asn Glu Gly Gly Phe
                245                 250                 255
Val Glu Asp Thr Leu Lys Ala Ile Asp Gly Arg Val Ile His Thr Tyr
                260                 265                 270
His Thr Glu Gly Ala Gly Gly Gly His Ala Pro Asp Ile Ile Lys Ala
            275                 280                 285
Ala Gly Phe Pro Asn Ile Leu Pro Ser Ser Thr Asn Pro Thr Arg Pro
290                 295                 300
Tyr Thr Ile Asn Thr Leu Glu Glu His Leu Asp Met Leu Met Val Cys
305                 310                 315                 320
His His Leu Asp Ala Asn Ile Pro Glu Asp Ile Ala Phe Ala Asp Ser
                325                 330                 335
Arg Ile Arg Lys Glu Thr Ile Ala Ala Glu Asp Val Leu His Asp Leu
            340                 345                 350
Gly Val Phe Ser Met Ile Ser Ser Asp Ser Gln Ala Met Gly Arg Val
            355                 360                 365
Gly Glu Val Ile Ile Arg Thr Trp Gln Thr Ala Asp Lys Met Lys Lys
370                 375                 380
Gln Arg Gly Lys Leu Gln Glu Asp Asn Gly Val Gly Asp Asn Phe Arg
385                 390                 395                 400
Val Lys Arg Tyr Ile Ala Lys Tyr Thr Ile Asn Pro Ala Ile Ala His
                405                 410                 415
```

Gly Ile Ala Asp Tyr Val Gly Ser Val Glu Val Gly Lys Leu Ala Asp
              420                 425                 430

Leu Val Val Trp Asn Pro Ala Phe Phe Gly Val Lys Pro Glu Leu Val
              435                 440                 445

Leu Lys Gly Gly Met Ile Ala Tyr Ser Thr Met Gly Asp Pro Asn Ala
        450                 455                 460

Ser Ile Pro Thr Pro Gln Pro Val Leu Tyr Arg Pro Met Phe Ala Ala
465                 470                 475                 480

Lys Gly Asp Ala Lys Tyr Gln Thr Ser Ile Thr Phe Val Ser Lys Ala
              485                 490                 495

Ala Tyr Glu Lys Gly Ile His Glu Gln Leu Gly Leu Lys Lys Lys Val
              500                 505                 510

Lys Pro Val His Gly Ile Arg Lys Leu Thr Lys Lys Asp Leu Ile Leu
        515                 520                 525

Asn Asp Lys Thr Pro Lys Ile Asp Val Asp Pro Gln Thr Tyr Glu Val
        530                 535                 540

Lys Val Asp Gly Gln Leu Val Thr Cys Glu Pro Ala Glu Ile VaL Pro
545                 550                 555                 560

Met Ala Gln Arg Tyr Phe Leu Phe
              565

(2) INFORMATION FOR SEQ ID NO:4:

(i) SEQUENCE CHARACTERISTICS:
        (A) LENGTH: 159 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Glu Lys Asn Glu Pro Ser Ala Leu Val Glu Leu Asp His Ile Leu Phe
1               5                   10                  15

Ala Ser Asn Val Ala Gln Glu Thr Arg Ser Gly Asn Gln Arg Met Gly
              20                  25                  30

Glu Arg Met Ala Lys Leu Cys Val Asp Leu Tyr Pro Ser Pro Ile Leu
        35                  40                  45

Ile Glu Tyr Thr Asn Arg Ile Lys Glu Lys Lys Ala Tyr Gly His Ser
    50                  55                  60

Ala Ile Val Phe Ala Ile Val Ala Tyr His Leu Lys Val Thr Lys Glu
65                  70                  75                  80

Thr Ala Val Gly Ala Tyr Leu Phe Ala Asn Val Ser Ala Leu Val Gln
              85                  90                  95

Asn Ala Val Arg Gly Ile Pro Ile Gly Gln Thr Asp Gly Gln Arg Ile
              100                 105                 110

Leu Val Glu Ile Gln Pro Leu Leu Glu Glu Gly Val Arg Thr Ile Ser
              115                 120                 125

Gln Leu Pro Lys Glu Asp Leu Gly Ala Val Ser Pro Gly Met Glu Ile
        130                 135                 140

Ala Gln Met Arg His Glu Arg Leu Asn Val Arg Leu Phe Met Ser
145                 150                 155

(2) INFORMATION FOR SEQ ID NO:5:

(i) SEQUENCE CHARACTERISTICS:
        (A) LENGTH: 207 amino acids
        (B) TYPE: amino acid
        (C) STRANDEDNESS: single
        (D) TOPOLOGY: linear ( i i ) MOLECULE TYPE: peptide ( x i ) SEQUENCE DESCRIPTION: SEQ ID NO:5:

| Val | Arg | Asn | Val | Glu | Pro | Ile | Arg | Ile | Gly | Ile | Gly | Gly | Pro | Val | Gly |
|---|---|---|---|---|---|---|---|---|---|---|---|---|---|---|---|
| 1 | | | | 5 | | | | | 10 | | | | | 15 | |

| Ala | Gly | Lys | Thr | Met | Leu | Val | Glu | Lys | Leu | Thr | Arg | Ala | Met | His | Lys |
|---|---|---|---|---|---|---|---|---|---|---|---|---|---|---|---|
| | | | 20 | | | | 25 | | | | | 30 | | | |

| Glu | Leu | Ser | Ile | Ala | Val | Val | Thr | Asn | Asp | Ile | Tyr | Thr | Lys | Glu | Asp |
|---|---|---|---|---|---|---|---|---|---|---|---|---|---|---|---|
| | | 35 | | | | | 40 | | | | | 45 | | | |

| Ala | Gln | Phe | Leu | Leu | Lys | His | Gly | Val | Leu | Pro | Ala | Asp | Arg | Val | Ile |
|---|---|---|---|---|---|---|---|---|---|---|---|---|---|---|---|
| | 50 | | | | | 55 | | | | | 60 | | | | |

| Gly | Val | Glu | Thr | Gly | Gly | Cys | Pro | His | Thr | Ala | Ile | Arg | Glu | Asp | Ala |
|---|---|---|---|---|---|---|---|---|---|---|---|---|---|---|---|
| 65 | | | | | 70 | | | | | 75 | | | | | 80 |

| Ser | Met | Asn | Phe | Pro | Ala | Ile | Asp | Glu | Leu | Lys | Glu | Arg | His | Pro | Asp |
|---|---|---|---|---|---|---|---|---|---|---|---|---|---|---|---|
| | | | | 85 | | | | | 90 | | | | | 95 | |

| Leu | Glu | Leu | Ile | Phe | Ile | Glu | Ser | Gly | Gly | Asp | Asn | Leu | Ala | Ala | Thr |
|---|---|---|---|---|---|---|---|---|---|---|---|---|---|---|---|
| | | | 100 | | | | | 105 | | | | | 110 | | |

| Phe | Ser | Pro | Glu | Leu | Val | Asp | Phe | Ser | Ile | Tyr | Ile | Ile | Asp | Val | Ala |
|---|---|---|---|---|---|---|---|---|---|---|---|---|---|---|---|
| | | 115 | | | | | 120 | | | | | 125 | | | |

| Gln | Gly | Glu | Lys | Ile | Pro | Arg | Lys | Gly | Gly | Gln | Gly | Met | Ile | Lys | Ser |
|---|---|---|---|---|---|---|---|---|---|---|---|---|---|---|---|
| | 130 | | | | | 135 | | | | | 140 | | | | |

| Val | Leu | Phe | Ile | Ile | Asn | Lys | Ile | Asp | Leu | Ala | Pro | Tyr | Val | Gly | Ala |
|---|---|---|---|---|---|---|---|---|---|---|---|---|---|---|---|
| 145 | | | | | 150 | | | | | 155 | | | | | 160 |

| Ser | Leu | Glu | Val | Met | Glu | Arg | Asp | Thr | Leu | Ala | Ala | Arg | Gly | Asp | Lys |
|---|---|---|---|---|---|---|---|---|---|---|---|---|---|---|---|
| | | | | 165 | | | | | 170 | | | | | 175 | |

| Pro | Tyr | Ile | Phe | Thr | Asn | Leu | Lys | Asp | Glu | Ile | Gly | Leu | Ala | Glu | Val |
|---|---|---|---|---|---|---|---|---|---|---|---|---|---|---|---|
| | | | 180 | | | | | 185 | | | | | 190 | | |

| Leu | Glu | Trp | Ile | Lys | Thr | Asn | Ala | Leu | Leu | Tyr | Gly | Leu | Glu | Ser | |
|---|---|---|---|---|---|---|---|---|---|---|---|---|---|---|---|
| | | 195 | | | | | 200 | | | | | 205 | | | |

( 2 ) INFORMATION FOR SEQ ID NO:6:

( i ) SEQUENCE CHARACTERISTICS:
( A ) LENGTH: 270 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:6:

| Lys | Cys | Thr | Gly | Val | Leu | Gln | Leu | Ser | Ala | Ala | Lys | Lys | Arg | Gln | Lys |
|---|---|---|---|---|---|---|---|---|---|---|---|---|---|---|---|
| 1 | | | | 5 | | | | | 10 | | | | | 15 | |

| Thr | Ile | Ile | Ser | Ser | Cys | Tyr | His | Glu | Gly | Ala | Leu | Lys | Val | Ser | Arg |
|---|---|---|---|---|---|---|---|---|---|---|---|---|---|---|---|
| | | | 20 | | | | | 25 | | | | | 30 | | |

| Pro | Ile | Tyr | Leu | Glu | Lys | Asp | Leu | Pro | Phe | Leu | Tyr | Leu | Ile | His | Val |
|---|---|---|---|---|---|---|---|---|---|---|---|---|---|---|---|
| | | | 35 | | | | | 40 | | | | | 45 | | |

| Gly | Gly | Gly | Tyr | Val | Asp | Gly | Asp | Val | Tyr | Leu | Thr | Asn | Leu | Asp | Val |
|---|---|---|---|---|---|---|---|---|---|---|---|---|---|---|---|
| | 50 | | | | | 55 | | | | | 60 | | | | |

| Glu | Glu | Glu | Ala | Glu | Leu | Ala | Val | Thr | Thr | Gln | Ser | Ala | Thr | Lys | Val |
|---|---|---|---|---|---|---|---|---|---|---|---|---|---|---|---|
| 65 | | | | | 70 | | | | | 75 | | | | | 80 |

| Tyr | Lys | Thr | Pro | Lys | Lys | Pro | Val | Val | Gln | Gln | Thr | Asn | Ile | His | Leu |
|---|---|---|---|---|---|---|---|---|---|---|---|---|---|---|---|
| | | | | 85 | | | | | 90 | | | | | 95 | |

| Lys | Lys | Gly | Ser | Val | Leu | Glu | Tyr | Leu | Leu | Asp | Pro | Leu | Ile | Ser | Tyr |
|---|---|---|---|---|---|---|---|---|---|---|---|---|---|---|---|
| | | | 100 | | | | | 105 | | | | | 110 | | |

| Lys | Gly | Ala | Arg | Phe | Ile | Gln | Glu | Thr | Thr | Val | His | Ile | Glu | Glu | Asp |
|---|---|---|---|---|---|---|---|---|---|---|---|---|---|---|---|
| | | | 115 | | | | | 120 | | | | | 125 | | |

| Ser | Gly | Phe | Phe | Tyr | Ser | Asp | Val | Ile | Thr | Pro | Gly | Trp | Ala | Glu | Asp |

```
                  130                     135                       140
Gly  Ser  Leu  Phe  Pro  Tyr  Asp  Trp  Ile  Arg  Ser  Lys  Leu  Lys  Val  Tyr
145                      150                      155                       160

Lys  Lys  Asp  Arg  Leu  Val  Leu  Phe  Asp  His  Leu  Arg  Leu  Glu  Pro  Asp
                    165                 170                      175

Glu  Asp  Met  Ser  Gly  Met  Leu  Gln  Met  Asp  Gly  Tyr  Thr  His  Ile  Gly
                180                      185                     190

Thr  Phe  Leu  Ile  Phe  His  Gln  Lys  Ala  Asp  Lys  Thr  Phe  Leu  Asp  Arg
               195                  200                      205

Leu  Tyr  Asp  Glu  Met  Glu  Ala  Phe  Asp  Ser  Asp  Val  Arg  Phe  Gly  Met
     210                      215                 220

Thr  Ser  Leu  Pro  Ala  Ser  Gly  Ile  Ile  Leu  Arg  Ile  Leu  Ala  Arg  Ser
225                      230                      235                       240

Thr  Gly  Ile  Ile  Glu  Asn  Met  Ile  Ser  Arg  Ala  His  Ser  Phe  Ala  Arg
               245                       250                      255

Arg  Glu  Leu  Leu  Gly  Lys  Asn  Gly  Val  Thr  Trp  Arg  Lys  Tyr
                260                      265                      270
```

(2) INFORMATION FOR SEQ ID NO:7:

(i) SEQUENCE CHARACTERISTICS:
  (A) LENGTH: 222 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:7:

```
Asp  Gln  Val  Asp  Leu  Leu  Ser  Ile  Leu  Thr  Leu  Gly  Phe  Val  Leu  Gly
1                   5                   10                       15

Ile  Lys  His  Ala  Met  Glu  Pro  Asp  His  Val  Ile  Ala  Val  Ser  Thr  Ile
               20                       25                      30

Val  Cys  Gln  Ser  Lys  Lys  Leu  Trp  Arg  Ser  Ser  Leu  Ala  Gly  Val  Phe
               35                       40                      45

Trp  Gly  Ile  Gly  His  Thr  Ser  Thr  Leu  Leu  Ile  Phe  Gly  Met  Thr  Ile
     50                      55                       60

Ile  Leu  Met  Lys  Lys  Lys  Ile  Ser  Gln  Glu  Trp  Ser  Met  Ser  Leu  Glu
65                       70                      75                        80

Phe  Leu  Val  Gly  Ile  Ile  Leu  Val  Tyr  Phe  Gly  Ile  Ser  Ala  Ile  Leu
                    85                      90                       95

Ser  Leu  Lys  Lys  Thr  His  Glu  His  Ser  His  Ser  Arg  Leu  His  Leu  His
                    100                     105                      110

Thr  Asp  His  Pro  Ile  Tyr  Thr  Tyr  Lys  Gly  Ile  Pro  Tyr  Val  Lys  Ser
               115                      120                     125

Leu  Phe  Ile  Gly  Ile  Ile  His  Gly  Leu  Ala  Gly  Ser  Ala  Ala  Met  Val
     130                     135                      140

Leu  Leu  Thr  Met  Ser  Thr  Val  Glu  Lys  Ala  Trp  Glu  Gly  Leu  Leu  Tyr
145                      150                      155                       160

Ile  Leu  Phe  Phe  Gly  Ala  Gly  Thr  Val  Leu  Gly  Met  Leu  Ser  Phe  Thr
                165                      170                     175

Thr  Leu  Ile  Gly  Ile  Pro  Phe  Thr  Leu  Ser  Ala  Arg  Lys  Ile  Arg  Ile
               180                      185                     190

His  Asn  Ala  Phe  Ile  Gln  Ile  Thr  Gly  Phe  Ile  Ser  Thr  Val  Phe  Gly
               195                      200                     205

Ile  His  Tyr  Met  Tyr  Asn  Leu  Gly  Val  Thr  Asp  Arg  Leu  Ile
               210                      215                     220
```

( 2 ) INFORMATION FOR SEQ ID NO:8:

( i ) SEQUENCE CHARACTERISTICS:
        ( A ) LENGTH: 6131 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:8:

| | | | | | | |
|---|---|---|---|---|---|---|
| CCCGGGATTA | TGTTTATCAC | ATATTATCAG | TATAGTTTAT | GCTTTTTTAA | AGGTTGGACG | 60 |
| GTTCTTGCTT | TCGTCTGGTT | AATGGTAGCC | GGTATTTTCA | TCACGATCAG | ACCGTTGATG | 120 |
| GAGCTTTTTA | AGAAAGATCA | ATAATATATC | GCAAAAAATA | TTTTAAAAAA | TCGCAGTTGC | 180 |
| TAGCGGGTTT | GTAAAATGAG | TGAGAATCTG | TTGGATGTAT | TAGAAGGAAA | TTTGATATAA | 240 |
| TTATTAGACG | AAAAATTCTA | AATATTCGAT | CTGTGAATGG | AGATTACAA | GATCAATTTC | 300 |
| ATAGTTTGGA | ACAAGCACTT | AAAATAGGAG | GTTATCCATG | AAACTGACTT | CACGTGAAAT | 360 |
| GGAAAAGCTC | ATGATTGTAG | TGGCGGCTGA | CTTGGCCCGC | CGTCGTAAAG | AGCGGGGCTT | 420 |
| AAAATTAAAT | TATCCTGAAG | CTGTCGCAAT | GATTACATAT | GAAGTGCTGG | AGGGGCGCG | 480 |
| GGATGGAAAA | ACGGTAGCTC | AGTTAATGCA | ATACGGTGCA | ACGATTCTTA | CAAAAGAAGA | 540 |
| TGTAATGGAA | GGGGTTGCCG | AAATGATCCC | GGATATTCAA | ATTGAGGCAA | CCTTTCCTGA | 600 |
| TGGAACAAAG | CTTGTCACGG | TTCATGACCC | GATCCGTTAA | ATGAGGAGGA | CGTACGATGA | 660 |
| TACCAGGGGA | GTATGTATTA | AAAAAGAAC | CTATTTATG | CAATCAAAAT | AAGCAGACGA | 720 |
| TCAAGATTCG | CGTGTTAAAC | CGGGGCGATC | GACCTGTTCA | GGTTGGTTCC | CATTTTCATT | 780 |
| TTTTTGAAGT | GAATCAATCG | CTTCAATTTC | ATCGTGAAAA | AGCATTTGGC | ATGCGTTTGA | 840 |
| ATATTCCGGC | TGGAACGGCG | GTTCGCTTCG | AGCCCGGAGA | TGCGAAAGAA | GTAGAAATAA | 900 |
| TTCCATTTTC | AGGTGAACGC | AAAGTGTATG | GTTTAAATAA | TGTAACGAAT | GGATCAGTTG | 960 |
| AAATGGGGAA | AAGAAATGA | GTTTTCGAT | GTCTCGAAAG | CAATATGCGG | ATATGTTTGG | 1020 |
| ACCAACTGTC | GGCGACGCCA | TTCGTTTGGC | AGATTCAGAA | TTGTTTATCG | AAATTGAAAA | 1080 |
| GGACTATACA | ACGTATGGAG | ATGAGGTAAA | GTTGGCGGC | GGCAAGGTGA | TCCGAGATGG | 1140 |
| AATGGGGCAG | CATCCTTTGG | CGACAAGCGA | TGAATGCGTC | GATCTCGTAT | TAACAAATGC | 1200 |
| GATTATTGTT | GATTACACAG | GTATTTATAA | AGCAGATATC | GGCATAAAAG | ATGGAATGAT | 1260 |
| TGCCTCCATA | GGAAAAGCGG | GGAACCCGTT | GTTAATGGAC | GGGGTCGATA | TGGTGATTGG | 1320 |
| AGCAGCAACA | GAAGTCATAG | CCGCAGAAGG | GATGATTGTG | ACAGCCGGAG | AATAGATGC | 1380 |
| TCATATTCAC | TTTATTTGCC | CTCAGCAAAT | CGAAACCGCT | CTTGCATCGG | GTGTGACCAC | 1440 |
| TATGATTGGC | GGAGGAACAG | GACCCGCTAC | AGGCACAAAT | GCCACTACTT | GTACACCGGG | 1500 |
| GCCTTGGAAT | ATCCATCGTA | TGCTTCAAGC | AGCCGAAGAA | TTCCCGATAA | ACTTGGGCTT | 1560 |
| TTAGGAAAG | GGAAACTGTT | CAGATGAGGC | TCCTTTAAAG | GAACAAATTG | AAGCGGGAGC | 1620 |
| GGTGGGATTA | AAGCTTCACG | AAGATTGGGG | ATCGACGGCG | GCGGCTATTG | ATACATGTTT | 1680 |
| GAAAGTGGCG | GATCGATATG | ATGTGCAAGT | AGCGATTCAT | ACAGACACTT | TAAATGAAGG | 1740 |
| CGGATTTGTC | GAGGATACTT | TGAAAGCCAT | AGACGGTCGA | GTGATTCATA | CCTATCATAC | 1800 |
| AGAAGGGGCT | GGCGGGGAC | ATGCTCCGGA | TATTATAAAA | GCGGCCGGCT | TCCCGAATAT | 1860 |
| TTTGCCTTCT | TCCACGAATC | CAACTCGACC | TTATACTATC | AATACTTTGG | AAGAGCATTT | 1920 |
| AGATATGTTA | ATGGTTTGCC | ACCACCTAGA | CGCTAATATT | CCAGAGGATA | TTGCTTTTGC | 1980 |
| CGATTCACGC | ATACGGAAAG | AGACCATCGC | GGCGGAAGAT | GTTTTACATG | ATTTAGGCGT | 2040 |
| TTTCAGCATG | ATTTCGTCTG | ATTCACAGGC | GATGGGGCGA | GTAGGAGAAG | TGATCATTCG | 2100 |

-continued

| | | | | | |
|---|---|---|---|---|---|
| TACGTGGCAA | ACGGCTGACA | AGATGAAAAA | GCAAAGAGGG | AAGTTACAAG | AAGACAATGG 2160 |
| TGTGGGAGAC | AACTTTCGTG | TGAAACGTTA | TATTGCCAAA | TATACGATCA | ATCCGGCCAT 2220 |
| TGCTCATGGT | ATTGCGGATT | ATGTGGGTTC | TGTTGAAGTG | GGAAAATTAG | CTGATTTAGT 2280 |
| GGTGTGGAAT | CCTGCTTTTT | TTGGTGTGAA | ACCTGAACTG | GTCTTAAAAG | GAGGAATGAT 2340 |
| TGCTTACAGC | ACTATGGGAG | ATCCCAATGC | CAGCATTCCG | ACACCGCAGC | CGGTTTTATA 2400 |
| TCGTCCGATG | TTTGCAGCGA | AAGGAGATGC | CAAATATCAA | ACGTCTATCA | CCTTTGTTTC 2460 |
| GAAAGCAGCG | TATGAAAAAG | GCATTCATGA | ACAGTTGGGT | TTGAAGAAAA | AGGTGAAACC 2520 |
| AGTCCATGGA | ATTCGAAAAT | TGACGAAAAA | AGATTTAATT | TTGAACGATA | AAACCCCAAA 2580 |
| AATTGACGTC | GATCCTCAGA | CATATGAAGT | AAAGGTAGAC | GGTCAATTAG | TGACATGTGA 2640 |
| ACCGGCAGAA | ATCGTCCCTA | TGGCACAACG | GTATTTCTTA | TTTTGAGGTG | AGAAAAACAT 2700 |
| GATGGTTGAA | AAAGTAGTCG | GAAACATCAC | GACATTAGAG | AAAAGAGTTC | CACATATAGA 2760 |
| ACGGGTTTAT | ATGCGAAGCG | ATGATTTAGT | CAAACGGGTG | AAACGGGTTG | TGACAGATCA 2820 |
| TGGCAAAGAG | ATTGGCATTC | GCTTAAAAGA | ACATCAGGAA | TTACAAGATG | GAGATATTTT 2880 |
| ATACATGGAC | GATCACAATA | TGATTGTGAT | ATCGGTCTTA | GAAGATGATG | TATTAACGAT 2940 |
| CAAACCAACA | TCCATGCAGC | AAATGGGGGA | AATTGCGCAC | AACTTGGCAA | TCGGCATTTG 3000 |
| CCGGCGCAGT | TTGAAGGAAA | TGAAATGATT | GTGCAATATG | ACTATTTAGT | AGAAGAACTG 3060 |
| CTTCAGAAGC | TATCGATTCC | ATTTACACGT | GAAAACAGAA | AAATGAAACA | AGCATTTCGC 3120 |
| CCAATAGGAC | ATCGTCATGA | ATAGATTACT | TTCACTTTTT | CAGTTGTGTG | ATTCCAACTT 3180 |
| TCCATCGGGA | TCGTTTTCTC | ACTCTTTTGG | ATTTTGGAAA | CATACATTCA | AGAAAAAGTG 3240 |
| ATCACGGATA | AAGAAAGCTT | TAAGAATGCT | ATTTCCGTTT | ATATCGGAAA | CAGCTGTTTT 3300 |
| TCACAGAAGG | CCTTGCTTGC | ATACTGGCTT | ATGAAGCAAT | GGAAAAAAAT | GAACCATCCG 3360 |
| CGTTGGTAGA | GCTTGATCAT | ATTTTATTTG | CATCGAACGT | TGCGCAAGAA | ACAAGAAGCG 3420 |
| GGAATCAAAG | GATGGGGGAA | CGGATGGCCA | AGCTATGTGT | GGATCTGTAT | CCATCTCCTA 3480 |
| TTTTAATAGA | ATATACAAAC | CGGATAAAAG | AAAAGAAAGC | GTATGGTCAT | TCTGCCATAG 3540 |
| TGTTTGCGAT | TGTCGCTTAC | CACTTAAAGG | TGACAAAGGA | AACGGCAGTC | GGAGCCTATT 3600 |
| TATTTGCCAA | TGTATCTGCT | CTTGTGCAAA | ATGCGGTGCG | TGGAATTCCG | ATTGGTCAAA 3660 |
| CAGACGGTCA | AAGGATCTTA | GTTGAAATTC | AACCTCTTTT | AGAGGAAGGG | GTAAGAACGA 3720 |
| TTTCACAATT | GCCTAAAGAG | GATTTAGGAG | CGGTAAGTCC | CGGGATGGAA | ATTGCTCAAA 3780 |
| TGCGCCATGA | ACGTTTAAAT | GTGCGCTTAT | TTATGTCTTA | AAATTCGGAA | TATAAGGAGT 3840 |
| GAGAAACGTG | GAACCAATAC | GTATTGGAAT | CGGAGGGCCT | GTTGGAGCGG | AAAAACGAT 3900 |
| GCTTGTGGAA | AAATTGACGA | GAGCCATGCA | TAAAGAATTG | AGCATCGCCG | TTGTGACAAA 3960 |
| TGATATCTAT | ACGAAGAAG | ATGCTCAATT | TCTTCTGAAG | CATGGTGTGC | TGCCGGCAGA 4020 |
| TCGCGTCATT | GGTGTGGAAA | CAGGAGGGTG | TCCGCATACA | GCTATTCGTG | AAGATGCATC 4080 |
| CATGAATTTT | CCCGCCATTG | ATGAACTAAA | AGAAAGGCAT | CCCGATCTTG | AGTTGATATT 4140 |
| TATCGAAAGC | GGCGGGGATA | ATCTAGCCGC | TACATTTAGT | CCGGAACTAG | TCGATTTCTC 4200 |
| TATTTACATT | ATTGATGTAG | CGCAAGGGGA | AAAAATTCCG | CGTAAAGGTG | GACAAGGGAT 4260 |
| GATTAAATCT | GTACTTTTTA | TCATCAATAA | AATTGATCTC | GCTCCGTACG | TTGGAGCCAG 4320 |
| TTTAGAGGTT | ATGGAGCGCG | ATACTCTGGC | AGCGAGAGGG | GATAAGCCAT | ATATTTTTAC 4380 |
| CAATTTAAAA | GATGAAATCG | GTCTTGCAGA | AGTATTGGAA | TGGATCAAAA | CCAATGCACT 4440 |
| ATTGTACGGA | TTGGAATCAT | GAAATGAAAT | GTACAGGAGT | ATTGCAGCTA | TCTGCCGCTA 4500 |
| AAAAGCGGCA | AAAAACCATT | ATCTCATCTT | GCTATCATGA | AGGGGCCTTA | AAAGTGAGCC 4560 |

| | | | | | |
|---|---|---|---|---|---|
| GTCCTATTTA | TCTTGAAAAG | GATCTACCTT | TCTTATATCT | CATTCATGTT | GGCGGAGGTT 4620 |
| ATGTAGACGG | GGATGTTTAT | TTAACCAATC | TTGATGTGGA | AGAAGAAGCT | GAGCTGGCGG 4680 |
| TTACAACGCA | ATCCGCTACA | AAGGTATATA | AACACCAAA | GAAGCCTGTA | GTTCAGCAAA 4740 |
| CGAACATTCA | TTTAAAGAAA | GGAAGCGTTC | TTGAATACTT | GCTGGATCCA | TTAATTTCTT 4800 |
| ATAAAGGAGC | ACGTTTTATA | CAAGAAACGA | CCGTTCATAT | AGAAGAGGAT | TCCGGTTTTT 4860 |
| TTTACAGCGA | TGTCATTACA | CCGGGTTGGG | CGGAAGATGG | GAGTTTGTTT | CCTTATGATT 4920 |
| GGATTCGTTC | GAAATTAAAA | GTATATAAAA | AGGACCGGCT | TGTGTTGTTT | GATCATTTAC 4980 |
| GGCTTGAGCC | GGATGAAGAT | ATGTCCGGAA | TGCTGCAAAT | GGACGGATAT | ACTCATATCG 5040 |
| GCACTTTTTT | GATCTTTCAT | CAGAAAGCAG | ATAAACATT | TCTTGACCGT | TTATATGATG 5100 |
| AAATGGAGGC | TTTTGATTCC | GACGTTCGAT | TTGGTATGAC | ATCATTGCCG | GCTAGCGGCA 5160 |
| TTATTTTACG | TATACTTGCA | CGTAGTACGG | GTATCATTGA | AACATGATT | TCTCGCGCTC 5220 |
| ATTCATTTGC | CAGACGAGAG | TTATTAGGCA | AGAATGGTGT | CACTTGGCGA | AAGTATTGAA 5280 |
| AGATAGGGTG | AGGAATAAAT | GATATTAGGA | GGCTTATAGA | TGGACCAAGT | AGACTTGCTT 5340 |
| TCCATTTTAA | CTTTAGGATT | CGTTCTTGGA | ATAAACATG | CTATGGAGCC | GGATCATGTG 5400 |
| ATAGCTGTAT | CAACGATTGT | TTGTCAAAGT | AAAAAACTTT | GGAGATCCTC | TTTAGCTGGA 5460 |
| GTCTTTGGG | GGATCGGGCA | TACATCCACA | TTACTTATAT | TTGGAATGAC | TATTATTTTG 5520 |
| ATGAAGAAAA | AAATTTCACA | AGAATGGTCG | ATGTCATTAG | AGTTTTAGT | CGGAATCATA 5580 |
| CTCGTTTATT | TTGGAATTTC | AGCCATTCTT | TCTCTTAAGA | AAACGCATGA | ACATTCCCAT 5640 |
| TCACGTCTTC | ATCTTCATAC | AGATCATCCT | ATTTATACAT | ATAAAGGGAT | TCCCTATGTT 5700 |
| AAATCTCTTT | TTATTGGGAT | CATTCATGGA | CTTGCCGGAA | GTGCAGCCAT | GGTATTGTTG 5760 |
| ACAATGAGTA | CAGTAGAAAA | GGCATGGGAA | GGTCTTCTTT | ATATTCTGTT | TTTTGGCGCC 5820 |
| GGAACGGTTT | TAGGCATGCT | TTCGTTTACG | ACTTTAATTG | GAATCCCATT | TACACTGAGT 5880 |
| GCCAGAAAGA | TTCGTATTCA | CAATGCCTTC | ATTCAAATAA | CGGGATTCAT | CAGCACGGTA 5940 |
| TTCGGAATTC | ATTATATGTA | TAATTTAGGT | GTAACCGATA | GGCTTATTTA | AACTTTGGAT 6000 |
| ACGGTAAATG | GGAACAAGAA | AATGTTTTTT | GCTGCATCAT | CATGATAAGA | TCATTCGTTC 6060 |
| CATCATAATG | GCGAACGGTA | TTAAAAACTA | TTGGCAGGAT | GATGGGCGGT | TTGACAGATG 6120 |
| CTCGGAGATC | T 6131 | | | | |

( 2 ) INFORMATION FOR SEQ ID NO:9:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal fragment ( x i ) SEQUENCE DESCRIPTION: SEQ ID NO:9:

Xaa Phe Xaa Met Xaa Xaa Lys Glu Tyr Ala Asp Met Phe Gly Pro Thr
1               5                   10                  15

Val Gly Asp Ala Ile Xaa Leu Ala
            20

( 2 ) INFORMATION FOR SEQ ID NO:10:

( i ) SEQUENCE CHARACTERISTICS:
        ( A ) LENGTH: 18 amino acids
        ( B ) TYPE: amino acid
        ( C ) STRANDEDNESS: single (D) TOPOLOGY: linear (ii) MOLECULE TYPE: peptide (v) FRAGMENT TYPE: N-terminal fragment (xi) SEQUENCE DESCRIPTION: SEQ ID NO:10:

```
Met Ile Pro Gly Glu Tyr Val Leu Lys Lys Glu Pro Ile Leu Xaa Asn
1               5                   10                  15
Xaa Asn
```

(2) INFORMATION FOR SEQ ID NO:11:

(i) SEQUENCE CHARACTERISTICS:
(A) LENGTH: 21 amino acids
(B) TYPE: amino acid
(C) STRANDEDNESS: single
(D) TOPOLOGY: linear (ii) MOLECULE TYPE: peptide (v) FRAGMENT TYPE: N-terminal fragment (xi) SEQUENCE DESCRIPTION: SEQ ID NO:11:

```
Met Xaa Leu Thr Ser Xaa Glu Met Glu Lys Leu Ala Met Ile Val Val
1               5                   10                  15
Ala Ala Xaa Leu Ala
            20
```

(2) INFORMATION FOR SEQ ID NO:12:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:12:

GAR TAY GCN GAY ATG TTY GG   20

(2) INFORMATION FOR SEQ ID NO:13:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:13:

AAR AAR GAR CCN ATN YT   17

(2) INFORMATION FOR SEQ ID NO:14:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:14:

GAR ATG GAR AAR YTN ATG AT   20

What is claimed is:

1. An isolated structural Bacillus sp. TB-90 (FERM BP-795) urease gene, which comprises base sequences encoding the amino acid sequences of three subunits of urease as defined in the Sequence Listing by SEQ ID NO:1, SEQ ID NO:2 and SEQ ID NO:3.

2. A recombinant DNA comprising a structural Bacillus sp. TB-90 (FERM BP-795) urease gene that replicates in *Escherichia coli*.

3. The recombinant DNA as defined in claim 2, wherein said urease gene comprises subunit base sequences encoding the amino acid sequences of three subunits of urease as defined in the Sequence Listing by SEQ ID NO:1, SEQ ID NO:2 and SEQ ID NO:3.

4. The recombinant DNA as defined in claim 2, which further comprises three open-reading-frame DNA sequences encoding the amino acid sequences in the Bacillus sp. TB-90 urease operon represented by SEQ ID NO:4, SEQ ID NO:5 and SEQ ID NO:6 in the Sequence Listing.

5. The recombinant DNA as defined in claim 4, which further comprises the open-reading-frame DNA sequence encoding the amino acid sequence represented by SEQ ID NO:7 in the Sequence Listing.

6. The recombinant DNA as defined in claim 2, which comprises the base sequence represented by SEQ ID NO:8 in the Sequence Listing.

7. A process for producing urease, which comprises cultivating *Escherichia coli* carrying a recombinant DNA comprising a structural Bacillus sp TB-90 (FERM BP-795) urease gene that replicates in *Escherichia coli* and recovering urease from the culture mixture.

8. The process for producing urease as defined in claim 7, wherein said urease gene comprises base sequences encoding the amino acid sequences of three subunits of the urease defined in the Sequence Listing by SEQ ID NO:1, SEQ ID NO:2 and SEQ ID NO:3.

9. The process for producing urease as defined in claim 7, wherein said recombinant DNA comprises the base sequence represented by SEQ ID NO:8 in the Sequence Listing.

10. The process for producing urease as defined in claim 7, wherein said *Escherichia coli* carrying said recombinant DNA is cultivated in a nitrogen-deficient medium.

11. The process for producing urease as defined in claim 7, wherein said recombinant DNA further comprises three open-reading-frame DNA sequences encoding the amino acid sequences in the Bacillus sp. TB-90 (FERM BP-795) urease operon represented by SEQ ID:4, SEQ ID NO:5 and SEQ ID NO:6 in the Sequence Listing.

12. The process for producing urease as defined in claim 11, wherein said recombinant DNA further comprises the open-reading-frame DNA sequence encoding the amino acid sequences represented by SEQ ID:7 in the Sequence Listing.

* * * * *

UNITED STATES PATENT AND TRADEMARK OFFICE
CERTIFICATE OF CORRECTION

PATENT NO. : 5,298,399
DATED : March 29, 1994
INVENTOR(S) : UOZUMI et al

It is certified that error appears in the above-identified patent and that said Letters Patent is hereby corrected as shown below:

Title page, left column, under [30] Foreign Application Priority Data, delete "2-10178" and insert --2-210178--.

Signed and Sealed this

Thirtieth Day of May, 1995

Attest:

BRUCE LEHMAN

*Attesting Officer*    *Commissioner of Patents and Trademarks*